United States Patent
Kuze et al.

(10) Patent No.: US 8,803,092 B2
(45) Date of Patent: Aug. 12, 2014

(54) QUANTUM INFRARED SENSOR AND QUANTUM INFRARED GAS CONCENTRATION METER USING THE SAME

(75) Inventors: Naohiro Kuze, Tokyo (JP); Seiichi Tokuo, Tokyo (JP); Yoshinori Yanagita, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 899 days.

(21) Appl. No.: 12/996,293

(22) PCT Filed: Jun. 4, 2009

(86) PCT No.: PCT/JP2009/060285
§ 371 (c)(1),
(2), (4) Date: Dec. 3, 2010

(87) PCT Pub. No.: WO2009/148134
PCT Pub. Date: Dec. 10, 2009

(65) Prior Publication Data
US 2011/0090505 A1    Apr. 21, 2011

(30) Foreign Application Priority Data

Jun. 4, 2008 (JP) ................. 2008-147261
Jul. 7, 2008 (JP) ................. 2008-176855

(51) Int. Cl.
*G01J 5/20* (2006.01)
*G01N 21/35* (2014.01)
*H01L 31/105* (2006.01)
*G01N 21/61* (2006.01)

(52) U.S. Cl.
CPC ............ *G01N 21/3504* (2013.01); *G01N 21/61* (2013.01); *H01L 31/105* (2013.01)
USPC .................................... 250/338.4

(58) Field of Classification Search
CPC ........................................ G01J 5/0205
USPC ...................................... 250/338.4
See application file for complete search history.

(56) References Cited

U.S. PATENT DOCUMENTS

| 4,158,133 | A | * | 6/1979 | Spaeth et al. ............. 250/214 R |
| 4,859,858 | A | | 8/1989 | Knodle et al. |
| 5,721,430 | A | | 2/1998 | Wong |
| 5,877,500 | A | * | 3/1999 | Braig et al. ................... 250/353 |
| 7,157,707 | B2 | * | 1/2007 | Ludwig ..................... 250/338.1 |

(Continued)

FOREIGN PATENT DOCUMENTS

| EP | 1667239 A1 | 6/2006 |
| JP | 61-030731 | * 2/1986 |

(Continued)

OTHER PUBLICATIONS

European Search Report issued Feb. 20, 2014, for corresponding European Application No. 09758401.5.

*Primary Examiner* — David Porta
*Assistant Examiner* — Mindy Vu
(74) *Attorney, Agent, or Firm* — Morgan, Lewis & Bockius LLP

(57) ABSTRACT

The present invention relates to a quantum infrared sensor and a gas concentration meter using the same, the quantum infrared sensor having a small and simple device shape and also being capable of performing stable measurement against disturbance changes such as changes in the flow amount and the temperature of gas to be measured. The quantum infrared sensor includes a pair of quantum infrared sensor elements, a pair of optical filters and a holding frame. The pair of optical filters is provided closer to an infrared light source than is the pair of quantum infrared sensor elements. The pair of optical filters is configured to selectively transmit infrared rays in specific different wavelength ranges, respectively. The pair of optical filters is housed in an upper level of the holding frame and provided while facing the pair of quantum infrared sensor elements through a pair of through holes, respectively.

17 Claims, 10 Drawing Sheets

(56) References Cited

U.S. PATENT DOCUMENTS

| | | |
|---|---|---|
| 2003/0116711 A1 | 6/2003 | Hara et al. |
| 2006/0157651 A1 | 7/2006 | Yamauchi et al. |
| 2007/0090337 A1 | 4/2007 | Ueno et al. |
| 2008/0179503 A1 | 7/2008 | Camargo et al. |

FOREIGN PATENT DOCUMENTS

| | | |
|---|---|---|
| JP | 8-75642 | 3/1996 |
| JP | 9-135010 | 5/1997 |
| JP | 2001-228022 | 8/2001 |
| JP | 2002-43554 | 2/2002 |
| JP | 2004-253534 | 9/2004 |
| JP | 2006-194791 | 7/2006 |
| WO | 9601418 A1 | 1/1996 |
| WO | WO 2005/027228 | 3/2005 |
| WO | WO 2006/095834 | 9/2006 |

* cited by examiner

QUANTUM INFRARED SENSOR AND QUANTUM INFRARED GAS CONCENTRATION METER USING THE SAME

RELATED APPLICATIONS

The present application is a U.S. National Phase Application of International Application No. PCT/JP2009/060285 (filed Jun. 4, 2009) which claims priority to Japanese Patent Application Nos. 2008-147261 (filed Jun. 4, 2008) and 2008-176855 (filed Jul. 7, 2008) which are hereby incorporated by reference in their entirety.

TECHNICAL FIELD

The present invention relates to a quantum infrared sensor and a quantum infrared gas concentration meter using the same. More specifically, the present invention relates to a quantum infrared sensor and a non-dispersive infrared gas concentration meter (hereinafter, referred to as an "NDIR gas concentration meter") using the same.

BACKGROUND ART

Heretofore, an NDIR gas concentration meter has been used as an infrared gas concentration meter for measuring the gas concentration in the atmosphere. Taking advantage of the fact that the absorbable wavelength of infrared ray (IR) differs depending on a gas type, the NDIR gas concentration meter measures the gas concentration through detection of the absorption amount. The NDIR gas concentration meter uses a filter, which transmits only an infrared ray having a wavelength corresponding to a detection target gas, and an infrared sensor in combination, and measures the gas concentration by measuring the absorption amount.

Here, an NDIR gas concentration meter which is reduced in size, highly accurate and capable of performing stable measurement in various environments is in demand. As an NDIR gas concentration meter of this kind, an infrared gas analyzer that measures the gas concentration in the atmosphere or the like by use of a wavelength selective infrared detection element has been proposed (refer to Patent Literature 1, for example).

Patent Literature 1 discloses an infrared gas sensor configured by integrally forming a wavelength selective filter selectively transmitting an infrared ray with a particular wavelength from a light source, and an infrared detector detecting the infrared rays that have passed through this wavelength selective filter. Specifically, Patent Literature 1 discloses an NDIR gas analyzer using a bolometer as an infrared sensor. The disclosed NDIR gas analyzer, however, employs a structure in which the infrared sensor is provided so as to float in the air inside a sealed chamber, and even requires vacuum sealing or inert gas sealing. Although Patent Literature 1 mentions that a quantum infrared detector is optionally usable, the literature neither discloses nor suggests a specific structure or embodiment for the quantum infrared detector.

In general, an infrared sensor is categorized into a thermal infrared sensor or a quantum infrared sensor. The thermal infrared sensor is a sensor that uses an infrared energy as heat and is an element that converts, into electric signals, effects (resistance change, capacitance change, electromotive force, spontaneous polarization) brought about by an increase in temperature when the temperature of the sensor itself rises due to the heat energy of the infrared rays. Such a thermal infrared sensor is categorized into a pyroelectric type (PZT, $LiTaO_3$), a thermoelectromotive force type (thermopile, thermocouple) or a conductive type (bolometer, thermistor). The thermal infrared sensors of these types have no wavelength dependency in the sensitivity thereof and require no cooling. However, the response rate is low and the detection capability is not very high. Meanwhile, the quantum infrared sensor is a sensor using electrons and holes generated by light photons when a semiconductor is irradiated with infrared rays. Such a quantum infrared sensor is categorized into a photoconductive type (such as HgCdTe), a photovoltaic type (such as InAs) or the like. Such quantum infrared sensors have a wavelength dependency in the sensitivity thereof and have advantages that the sensitivity is high and the response rate is high. However, the quantum infrared sensors need to be cooled. Thus, the quantum infrared sensors are generally used with a cooling mechanism such as a Peltier device or a stirling cooler. Accordingly, it has been difficult to apply the quantum infrared sensors to the aforementioned NDIR gas sensors.

In addition, in a case of using a thermal infrared sensor, the following structure is employed for the purpose of blocking heat. Specifically, an optical filter transmitting infrared rays is bonded to an opening portion of a can package. An infrared detection element detecting the infrared rays having passed through this optical filter is housed inside the can package.

Meanwhile, as a thermopile sensor, an infrared sensor in which an infrared detection element is placed in a molding resin instead of using a can package for simplification and an improvement in durability has been proposed (refer to Patent Literature 2, for example). The infrared sensor described in Patent Literature 2 includes: a flat plate-shaped optical filter selectively transmitting infrared light in a specific wavelength range; an infrared detection element including, on one of the surfaces thereof, a detection element portion for detecting infrared light having passed through the optical filter; and a support body which is provided between the optical filter and the detection-element-formed surface of the infrared detection element, and which also bonds together the optical filter and the infrared detection element while securing a predetermined gap between the optical filter and the detection-element-formed surface.

Specifically, Patent Literature 2 discloses a structure to achieve a reduction in size and weight of an infrared sensor by employing a simplified configuration without using a can package, and by providing an optical filter while a predetermined gap is secured on the detection-element-formed surface of the infrared sensor. In addition, Patent Literature 2 discloses that the embodiment uses a thermopile as the infrared sensor and employs a hollow structure. Moreover, it is described that the gap is secured so as to avoid damage on the infrared detection element of the infrared element or a scratch on the contact surface thereof.

Moreover, the support body described in Patent Literature 2 is provided only for the purpose of securing the gap, and has a function to prevent unnecessary light that has not passed through the optical filter from entering the infrared detection element through the gap, and also a function to prevent a scratch on the contact surface of the optical filter or the infrared detection element or damage on the infrared detection element. Accordingly, the support body has no function to hold the optical filter or no function for packaging.

In contrast, as described later in FIG. 7, a quantum infrared sensor according to the present invention has a structure in which a detection element surface is provided inside a molding resin and a surface to be in contact with an optical filter is the rear surface of the substrate of the detection element. Thus, the structure in which the optical filter and the infrared sensor are in contact with each other with no gap formed therebetween as shown in FIG. 6 is preferably used. Accordingly, a further reduction in size and thickness can be achieved.

Moreover, as described above, a quantum infrared sensor is an element converting infrared rays into electric signals by use of a photoconductive effect, photovoltaic effect or the like, and is generally used while being cooled. A quantum infrared sensor operable at room temperature has also been proposed (refer to Patent Literature 3, for example). The quantum infrared sensor described in Patent Literature 3 includes: a compound semiconductor sensor portion that detects infrared rays by use of a compound semiconductor layer provided on a substrate and then outputs electric signals; and an integrated circuit portion that performs an arithmetic operation on the electric signals outputted from the compound semiconductor sensor portion. In addition, the compound semiconductor sensor portion and the integrated circuit portion are housed in the same package. With this configuration, the quantum infrared sensor is less affected by electromagnetic noise or heat fluctuation, is allowed to perform detection at room temperature, and is also made reducible in size of the module.

Further, a quantum infrared sensor including, on a substrate, a quantum photoelectric conversion portion operable at room temperature has been proposed (refer to Patent Literature 4, for example). In this quantum infrared sensor, the quantum photoelectric conversion portion is packaged with a filter by a sealing resin.

However, Patent Literatures 3 and 4 described above disclose quantum infrared sensors, but do not disclose anything about application of the quantum infrared sensors to a gas sensor.

In other words, each of Patent Literatures 3 and 4 described above disclose a quantum infrared sensor operable at room temperature and packaged by resin, but does not state or suggest that the infrared sensor can be used in an NDIR gas concentration meter in combination with an optical filter and a holding frame.

In this respect, Patent Literature 5, for example, discloses a gas sensor using a quantum infrared sensor. The gas sensor described in Patent Literature 5 is a gas sensor in which a measurement cell and a reference cell are arranged in parallel. In addition, an optical filter corresponding to a measurement target component gas and a filter rotational chopper are provided between the cells and the quantum infrared sensor to detect a component concentration of a sample gas on the basis of a comparison between transmission amounts of infrared rays directed to the cells.

Here, Patent Literature 5 discloses that the quantum infrared sensor is applied to a gas sensor. However, a reduction in size is difficult in this case because the filter rotational chopper is used. In addition, Patent Literature 5 does not disclose anything about a specific configuration achieving a reduction in size by forming the infrared sensor element and the optical filter into a module and enabling a stable measurement against disturbance changes such as changes in the flow amount and temperature of the gas to be measured.

Specifically, Patent Literature 5 discloses an NDIR gas analyzer using a photoconductive infrared detection sensor. This infrared gas analyzer can detect the concentrations of multiple component gases by use of a single infrared sensor and a rotational chopper. However, Patent Literature 5 does not describe anything about a quantum infrared sensor configured by using a holding frame provided with multiple quantum infrared sensors, multiple optical filters and through holes as in the case of the quantum infrared sensor according to the present invention.

The NDIR gas concentration meter using a thermopile element has a problem that, when the temperature or flow amount of a gas to be measured changes to a large extent, the temperature of the sensor changes to a large extent, thus causing a large fluctuation in the output of the sensor. This leads to a problem that the gas concentration meter cannot perform practical measurement when used under the situation described above.

Meanwhile, in order to deal with the aforementioned significant change in the temperature of the sensor, a conventional infrared sensor element employs a method for easing the phenomenon by using a can package to thermally block and stabilizes a detection portion. Specifically, an air gap is provided around the sensor element and is also turned into a vacuum state or filled with a gas having a small thermal conductivity, or a heat sink portion having a large heat capacity is attached. However, such a configuration makes the element more complicated in shape and also larger in size and weight while requiring a high working accuracy for packaging. Thus, use of the aforementioned method causes an increase in cost.

Moreover, instead of using a can package, one using a package formed of a molding resin or the like, and one including a filter directly attached onto a surface of an infrared element have been proposed as well. However, a problem with these is that, when a thermal infrared sensor element is used, insufficient thermal isolation inhibits a stable measurement when the temperature of or the flow amount of a gas to be measured changes to a large extent.

Meanwhile, in a case where a conventional quantum infrared sensor is used, a method to thermally stabilize the element by use of a large heat sink or to cool the element by use of a Peltier device or liquid nitrogen is used because a stable, high sensitivity cannot be obtained at normal temperature. Here, a can package is used as in the case of a thermal infrared sensor for the purpose of preventing condensation due to the cooling of the element, for the purpose of enclosing the element with a gas having a low heat conductivity such as Xe or Ne for suppressing heat conduction to outside, or for other purposes. As a result, such a configuration involves an increase in the size of the element or complication of the shape of the element while requiring a high working accuracy for packaging. Thus, there arises a problem causing an increase in cost.

The present invention has been made in view of the aforementioned problems. Thus, an object of the present invention is to provide a quantum infrared sensor for an NDIR gas concentration meter and a quantum infrared gas concentration meter using the same, the quantum infrared sensor having a small and simple device shape and also being capable of performing stable measurement against disturbance changes such as changes in the flow amount and temperature of gas to be measured.

CITATION LIST

Patent Literature

PTL 1: Japanese Patent Laid-Open No. 2001-228022
PTL 2: Japanese Patent Laid-Open No. 2006-194791
PTL 3: International Patent Publication No. WO 2005/027228 Pamphlet
PTL 4: International Patent Publication No. WO 2006/095834 Pamphlet
PTL 5: Japanese Patent Laid-Open No. H08-75642 (1996)

SUMMARY OF INVENTION

The present invention has been made to achieve the object as above, and is characterized by comprising: a plurality of quantum infrared sensor elements; a plurality of optical filters, each one provided for a respective infrared sensor element, on the side directed to the infrared light source, and which selectively transmit infrared rays in specific different wavelength ranges, respectively; and a holding frame which holds at least the optical filters, and includes a plurality of through holes extending from the respective quantum infrared sensor elements toward the infrared light source, the quantum infrared sensor characterized in that the quantum infrared sensor elements and the filters are fitted into the through holes of the holding frame. (FIGS. 2A to 2C)

The quantum infrared sensor is characterized in that: the holding frame has a multilevel structure which comprises a lower level and an upper level and in which first and second ones of the through holes for receiving infrared rays are provided at each of the lower level and the upper level, the first and second through holes facing the quantum infrared sensor elements, respectively; first and second ones of the quantum infrared sensor elements are provided at the lower level; and first and second ones of the optical filters are provided at the upper level while facing the first and second quantum infrared sensor elements, respectively. (FIG. 2B)

The quantum infrared sensor is characterized in that the optical filters are formed of a pair of an optical filter transmitting reference light from the infrared light source, and an optical filter transmitting light in a wavelength range different from that of the reference light. (FIGS. 2A to 2C)

The quantum infrared sensor is characterized in that the optical filters are formed of an optical filter transmitting the reference light from the infrared light source, and a plurality of optical filters transmitting light rays in wavelength ranges each different from that of the reference light. (FIGS. 4A and 4B and FIGS. 5A to 5C)

The quantum infrared sensor is characterized in that the holding frame is formed of a previously molded package member.

The quantum infrared sensor is characterized in that the package member is formed so as to be surface-mountable by use of a terminal for surface mounting, which is provided to each of the quantum infrared sensor elements.

The quantum infrared sensor is characterized in that the optical filters and the quantum infrared sensor elements are in close contact with each other, respectively. (FIG. 6)

The quantum infrared sensor is characterized in that each of the quantum infrared sensor elements has a sensor element portion, and the sensor element portion comprises: a first contact layer provided on a substrate; an absorption layer provided on the first contact layer; a barrier layer provided on the absorption layer; a second contact layer provided on the barrier layer; a second electrode provided on the second contact layer; a passivation layer provided adjacent to the first contact layer, the absorption layer, the barrier layer and the second contact layer; and a first electrode provided on the substrate via the passivation layer. (FIG. 7)

The quantum infrared sensor is characterized in that the first contact layer is made of n-type InSb, the absorption layer is made of p-type doped InSb, the barrier layer is made of p-type AlInSb, and the second contact layer is made of p-type InSb. (FIG. 7)

The quantum infrared sensor is characterized in that a plurality of the sensor element portions are provided, and the plurality of the sensor element portions are connected in series. (FIG. 8)

A quantum infrared gas concentration meter is characterized by comprising: an infrared light source arranged at one end in a sample cell forming a flow passage of a measurement target gas; and the quantum infrared sensor according to any one of claims 1 to 10, which is arranged at the other end in the sample cell. (FIG. 9)

The quantum infrared gas concentration meter according is characterized by further comprising: subtraction means for receiving sensor signals inputted via amplifiers amplifying sensor signals from the quantum infrared sensors and filters removing noise, and for subtracting signals from a circuit offset memory from the sensor signals to remove offsets, respectively; arithmetic operation means for computing, on the basis of signals from the subtraction means, a ratio of a transmission light amount in an absorption band of the measurement target gas to a transmission light amount in a wavelength range non-absorbable by the measurement target gas; addition means for adding, to a signal from the arithmetic operation means, an offset corresponding to a proportional coefficient from a gas offset memory because of usage of two wavelength ranges; and division means for performing division of a signal from the addition means by a light absorption coefficient of the gas from a gas constant memory and a constant of a gas passage length, the quantum infrared gas concentration meter characterized in that quantity of gas concentration is determined by use of the transmission light amount in the absorption band of the measurement target gas and the transmission light amount in the wavelength range non-absorbable by the measurement target gas. (FIG. 10)

According to the present invention, the quantum infrared sensor includes: multiple quantum infrared sensor elements; multiple optical filters, each one provided for a respective infrared sensor element, on the side directed to the infrared light source, and which selectively transmit infrared rays in specific different wavelength ranges, respectively; and a holding frame which holds at least the optical filters, and includes a plurality of through holes extending from the respective quantum infrared sensor elements toward the infrared light source. In addition, the quantum infrared sensor elements and the filters are fitted into the through holes of the holding frame. Thus, it is possible to achieve a quantum infrared sensor for an NDIR gas concentration meter and a quantum infrared gas concentration meter using the same, the quantum infrared sensor having a small, thin and simple device shape and also being capable of performing stable measurement against disturbance changes such as changes in the flow amount and temperature of gas to be measured.

DESCRIPTION OF EMBODIMENTS

Hereinafter, examples of the present invention will be described by referring to the accompanying drawings.

Example 1

Figure 1A:
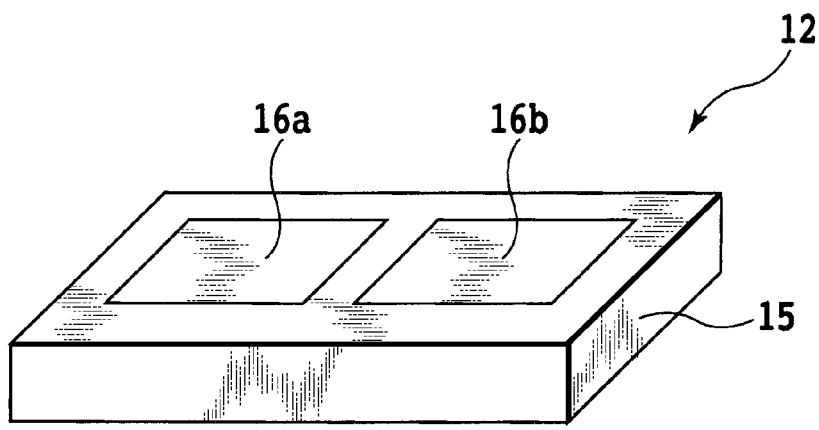
FIG. 1A is a configuration diagram of a quantum infrared sensor according to the present invention in Example 1 and is a top perspective view.
Figure 1B:
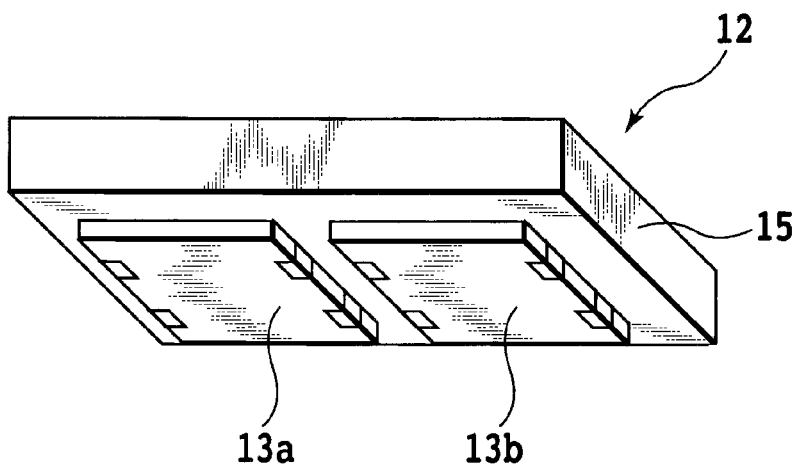
FIG. 1B is a configuration diagram of the quantum infrared sensor according to the present invention in Example 1 and is a bottom perspective view.
Figure 2A:
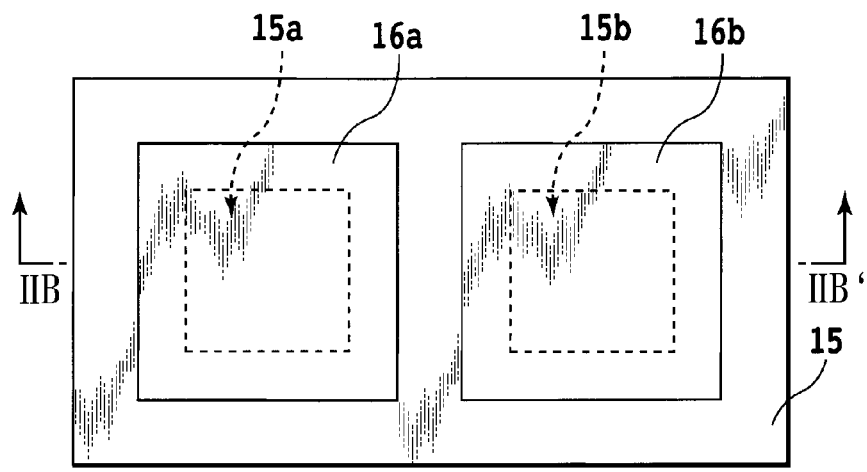
FIG. 2A is a configuration diagram of the quantum infrared sensor according to the present invention in Example 1 and shows a top view thereof.
Figure 2B:
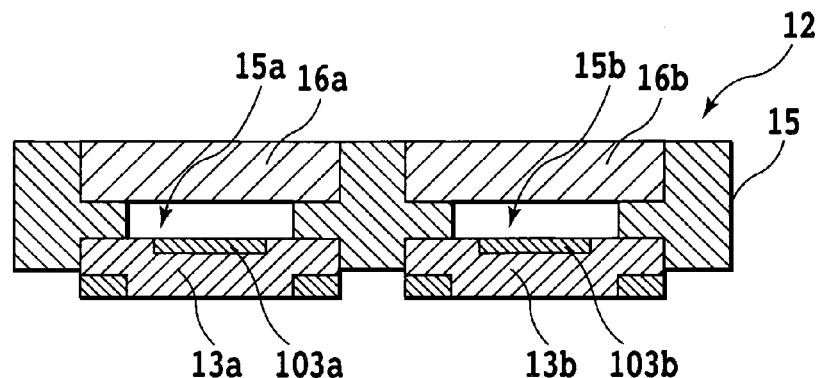
FIG. 2B is a configuration diagram of the quantum infrared sensor according to the present invention in Example 1 and shows a cross-sectional view thereof.
Figure 2C:
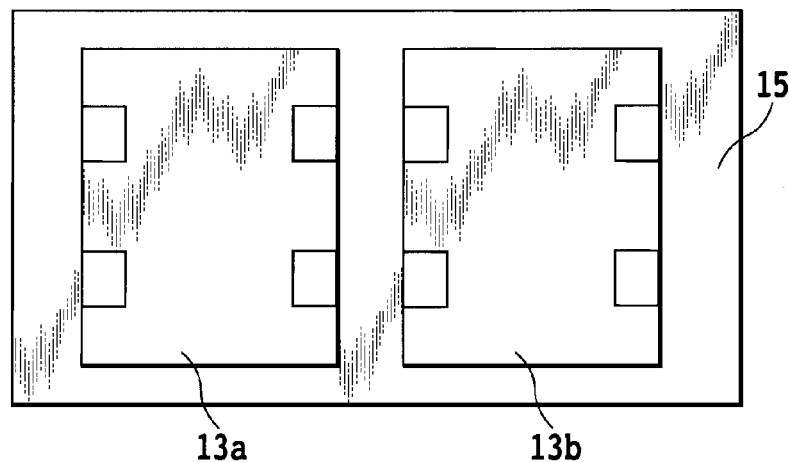
FIG. 2C is a configuration diagram of the quantum infrared sensor according to the present invention in Example 1 and shows a bottom view thereof.

FIGS. 1A and 1B and FIGS. 2A to 2C are configuration diagrams of a quantum infrared sensor according to the present invention in the case of Example 1. FIG. 1A is a top perspective view, and FIG. 1B is a bottom perspective view. FIGS. 2A to 2C show top, cross-sectional and bottom views, respectively. Note that, FIG. 2B is a cross-sectional view taken along the line IIB-IIB' in FIG. 2A.

A quantum infrared sensor 12 according to the present invention includes multiple quantum infrared sensor elements 13a and 13b, multiple optical filters 16a and 16b and a holding frame 15. The multiple optical filters 16a and 16b, are provided for the infrared sensor elements 13a and 13b, respectively, on the side directed to the infrared light source. The multiple optical filters 16a and 16b are configured to selectively transmit infrared rays in specific different wavelength ranges, respectively. The holding frame 15, which includes multiple through holes 15a and 15b, holds at least these optical filters 16a and 16b to which the quantum infrared sensor elements 13a and 13b are faced. Here, light receiving portions of the quantum infrared sensor elements 13a and 13b are shown by sensor element portions 103a and 103b, respectively.

The infrared sensor according to the present invention is a quantum infrared sensor. Thus, the through holes 15a and 15b only need to be formed so as to allow light to pass therethrough and do not have to be in a vacuum state. In addition, the through holes 15a and 15b do not have to be sealed with an inert gas, nitrogen gas or the like either. Accordingly, the structure configured of multiple infrared sensors elements, multiple optical filters and a holding frame as in the case of the present invention is very simple and can achieve a reduction in size and thickness.

As shown in FIG. 1A, a pair of the optical filters 16a and 16b is formed of a pair of an optical filter transmitting reference light from the infrared light source, and an optical filter transmitting light in a wavelength range different from that of the reference light.

Moreover, each optical filter selectively transmitting infrared light in a specific wavelength range, which is used in the present invention, uses an optical member transmitting electromagnetic waves such as infrared rays, thereby selectively transmitting infrared light in a specific wavelength range. Here, the optical member can be used alone if it has a function to selectively transmit infrared light in a specific wavelength range. Further, a dielectric multi-layered film filter obtained by vapor depositing, in a layered form, dielectrics having different reflective indices on the optical member is used.

An example of the optical filter is described below, but the optical filter in Example 1 is not limited to this example, and any optical filter having a function to selectively transmit infrared light is usable without being limited to this example. As an example of the optical filter, an optical filter having the following functions is used. Specifically, the optical filter has a function not to transmit infrared rays of a long wavelength or a short wavelength or neither one of the wavelengths by an optical member and a thin film formed of multiple layers on the optical filter. More specifically, an optical filter having a function to transmit only an infrared ray of a specific wavelength as a result of combining the aforementioned transmission functions is used.

A single filter may be used as the optical filter to achieve the function to transmit an infrared ray of a specific wavelength, while multiple filters may be used depending on situation. Moreover, as a material for the optical member, a material that transmit predetermined infrared rays, such as silicon (Si), silica glass ($SiO_2$), sapphire ($Al_2O_3$), Ge, ZnS, ZnSe, $CaF_2$ or $BaF_2$ is used. Further, as the thin film member to be vapor deposited on the aforementioned material, a material such as silicon (Si), silica glass ($SiO_2$), sapphire ($Al_2O_3$), Ge, ZnS, $TiO_2$, $MgF_2$, $SiO_2$, $ZrO_2$ or $Ta_2O_5$ is used. In addition, the dielectric multi-layered film filter obtained by stacking, in a layered form, dielectrics having different reflective indices one on top of another on the optical member may be formed on both surfaces of the optical member with different predetermined thicknesses on the front and rear surfaces, or may be formed only on one of the surfaces thereof. Further, for the purpose of preventing unnecessary reflection, an anti-reflective film may be formed on the uppermost layers of the both front and rear surfaces of the optical filter or the uppermost layer of one of the surfaces thereof.

The sizes of length and width of the optical filter used, in the present invention may be equal to or less than the sizes of the quantum infrared sensor element. More preferably, the size of the optical filter may be exactly the same as the size of the light receiving portion of the quantum infrared sensor element or may be large enough to cover the light receiving portion, for the purpose of reducing cost. Specifically, when the size of the light receiving portion is 0.7 mm×0.7 mm, the optical filter is formed to have the exactly same size, i.e., 0.7 mm×0.7 mm, or may be formed to have a slightly larger size, which is approximately 1 mm×1 mm, to allow a margin for fixing the optical filter. The thickness of the optical filter is preferably thin in order to reduce absorption of infrared rays by the optical filter itself. Specifically, the thickness of the optical filter is not greater than 0.8 mm, preferably, not greater than 0.5 mm, and more preferably, not greater than 0.4 mm.

In addition, as shown in FIG. 1B, as the quantum infrared sensor elements capable of detecting, at normal temperature, infrared rays having passed through the optical filters 16a and 16b, photovoltaic type sensors, photoconductive effect type sensors, photo-emissive effect type sensors and the like are available. Any of these types can be used in the present invention, but the photo-emissive effect type sensor has a problem that a special environment such as a high vacuum state is required, thus causing an increase in the size of the device itself or the sensor portion thereof. Meanwhile, the photoconductive effect type sensor conducts a current through the sensor itself, and therefore has a disadvantage that noise becomes large. It is thus difficult to perform measurement with high sensitivity at normal temperature. Accordingly, the photovoltaic type sensor is most preferable.

A configuration example of a quantum infrared sensor according to the present invention, which operates at normal temperature, is described below. However, the quantum infrared sensor capable of detecting infrared rays having passed through the optical filter is not limited to this example.

The quantum infrared sensor according to the present invention operating at normal temperature is a quantum infrared sensor in which each light receiving portion having a photodiode structure generating a photovoltaic effect by infrared rays is formed on a substrate. A single-crystal Si substrate, a glass substrate, a GaAs substrate or the like can be used as the substrate. Here, a semi-insulating GaAs substrate is used as an example.

Further, the light receiving portion is a quantum type light receiving portion in which a light receiving surface thereof is excited by infrared photons, and electric properties of the light receiving surface are changed by the excitation. In the light receiving portion, infrared energy is converted into electric energy by the photoelectric conversion on the light receiving surface. Because of the quantum type, the infrared detection sensitivity of the light receiving portion is barely affected by the heat capacity of the light receiving portion or of the area around the light receiving portion.

Moreover, the light receiving surface of the light receiving portion is made of $InAs_xSb_{1-x}$ ($0 \leq x \leq 1$), for example, and is capable of efficiently performing photoelectric conversion of infrared rays of a wavelength approximately from 1 to 11 μm. The light receiving portion is configured of a InSb-based quantum PIN photodiode formed on the semi-insulating GaAs substrate, for example.

Moreover, the InSb-based quantum PIN photodiode may include a substrate, an n-type InSb layer (contact layer) formed on this substrate, a p-type doped InSb layer (absorption layer) formed on this n-type InSb layer, a p-type AlInSb layer (barrier layer) formed on this p-type doped InSb layer and a p-type InSb layer (contact layer) formed on this p-type AlInSb layer (this configuration will be described later by referring to FIG. 7). Moreover, as an example of the configuration of the quantum infrared sensor of the present invention, which operates at normal temperature, the structure described in Patent Literature 4 may be used.

In sensor element portions (light receiving portions), PIN photodiodes are connected to each other in series by a connection wiring (the connection will be described later by referring to FIG. 8). When infrared rays enter from the rear surface side (i.e., a side opposite to the surface where the PIN photodiodes are formed) of the substrate, photovoltaic power corresponding to the amount of radiation of the infrared rays is generated in the PIN photodiodes, and the photovoltaic power is outputted to the outside of the light receiving portions through the connection wiring.

The sensitivity of the quantum infrared sensor operating at normal temperature is higher than that of a thermoelectromotive force element such as a thermopile generally used heretofore, and the amount of noise to signal, i.e., the SN ratio is also better than that of the thermoelectromotive force element. Moreover, the quantum infrared sensor can be formed in a surface-mountable form at the time of the assembly molding process.

The quantum infrared sensor elements 13a and 13b of the present invention are preferably used in a form of being packaged by resin for the purpose of achieving a reduction in size. Each of the quantum infrared sensor elements is preferably reduced in size, i.e., the quantum infrared sensor having a size not greater than 3 mm (length)×4 mm (width)×1 mm (thickness), more preferably, not greater than 2 mm (length)×3 mm (width) ×0.5 mm (thickness), or even more preferably, not greater than 1.5 mm (length)×2.5 mm (width)×0.4 mm (thickness) is used.

Further, the optical filters and the quantum infrared sensors operating at normal temperature are fixed to each other with gaps formed therebetween, thereby forming a filter attached quantum infrared sensor device. The method of fixing the optical filters and the quantum infrared sensors operating at normal temperature to each other is optionally selected.

Figure 3A:
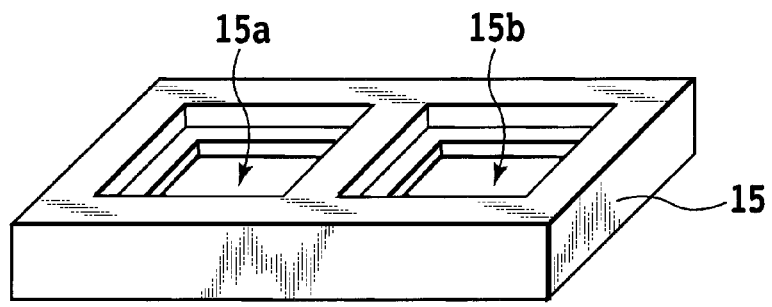
FIG. 3A is a configuration diagram of a holding frame of the quantum infrared sensor according to the present invention and is a top perspective view.
Figure 3B:
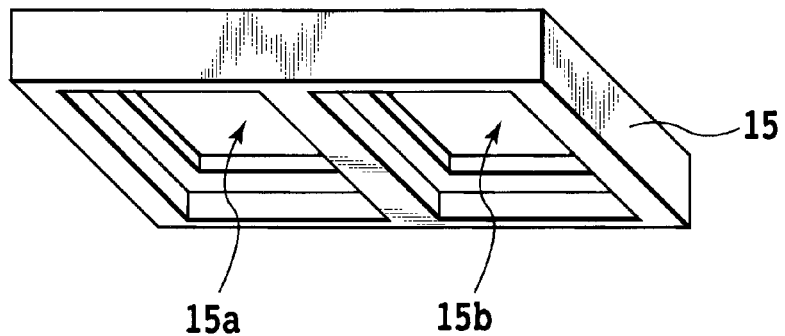
FIG. 3B is a configuration diagram of the holding frame of the quantum infrared sensor according to the present invention and is a bottom perspective view.

FIGS. 3A and 3B are configuration diagrams of the holding frame of the infrared sensor of the present invention. FIG. 3A is a top perspective view, and FIG. 3B is a bottom perspective view.

The holding frame 15 has a multilevel structure which includes a lower level and an upper level and in which the first and second through holes 15a and 15b for receiving infrared rays are provided at each of the lower and upper levels and an intermediate level therebetween, the first and second through holes 15a and 15b facing the first and second quantum infrared sensor elements 13a and 13b, respectively. The first and second quantum infrared sensor elements 13a and 13b are provided at the lower level. The first and second optical filters 16a and 16b are provided at the upper level while facing the first and second quantum infrared sensor elements 13a and 13b via the first and second through holes 15a and 15b, respectively.

In addition, the holding frame 15 is preferably a previously molded package member or a terminal attached package member molded and provided with terminals electrically connectable to the quantum infrared sensor elements. In addition, the package member is preferably formed so as to be surface-mountable by use of terminals for surface mounting, which are provided to each of the quantum infrared sensor elements.

Moreover, an electric component package member made of semi-insulating ceramic, resin or the like can be used as the package member forming the holding frame 15. Specifically, alumina, mullite, cordierite, steatite, aluminum nitride, silicon carbide, silicon or the like or a mixture of these substances is used as the ceramic. In addition, resin such as epoxy resin, silicon resin, phenol resin, polyimide resin, urethane resin or polyphenylene sulfide resin is used as the resin. Moreover, an additive such as a hardening agent, hardening accelerator, filler, release agent or modifying agent may be added to these.

In addition, when the connection terminals provided to the quantum infrared sensor elements themselves are directly used for surface mounting, metal that can be easily molded such as aluminum can be used for the holding frame. When metal is used for the holding frame, the connection terminals of the quantum infrared sensor elements need to be electrically insulated from the holding frame.

The aforementioned package member is molded into such a predetermined shape that the infrared sensor elements may be so arranged as to allow infrared rays having passed through the optical filters to arrive at the light receiving surfaces of the infrared sensor elements. The optical filters and the infrared sensor elements are fixed to the holding frame. The method for the fixing is not limited in particular. An adhesive or the like may be used for the adhesion of the components, or some attachment members may be fabricated with the same material as that of the package member and used for the fixing. Moreover, it is possible to employ a method using a fitting structure and thus using no particular adhesion.

In attaching the optical filters to the holding frame, the optical filters are attached to the holding frame in such a way that the upper surfaces of the optical filters are flush with the outer surface of the holding frame or located lower than the outer surface of the holding frame. If the optical filters protrude from the outer surface of the holding frame, disturbance light may enter from the side surfaces of the optical filters, and as a result, the optical filters may not function as accurate bandpass filters.

A barrier wall between the two through holes, which is formed as a result of forming the through holes in the holding frame, serves an important role. The barrier wall can prevent infrared rays having passed through the respective optical filters from interfering with each other and thus makes it possible to perform measurement of, with better accuracy, the amounts of infrared rays having passed through the bandpass filters.

The gap between each of the optical filters and a corresponding one of the quantum infrared sensor elements according to the present invention does not have to be in a hermetically sealed (hermetic) structure, a vacuum structure or a structure filled with a gas, and can be even formed so as to allow communication with external air. Such a structure is made possible since the quantum infrared sensor elements are not easily affected by the temperature of the external air or the moving speed of the external air because of the characteristics of the elements.

Moreover, the quantum infrared sensor can be surface-mountable by a solder reflow process or the like even after the quantum infrared sensor elements are packaged, by arranging the quantum infrared sensor elements, which are formed in a surface-mountable shape at the time of assembly, in such a way that the surface-mountable terminals protrude from the bottom surface of the molded package.

The entire size of the combination of the multiple optical filters and multiple quantum infrared sensor elements, which are fitted into the holding frame, according to the present invention can be smaller than ever before. Although the sizes of length and width change depending on the number of types of gases to be measured, when the device is formed of a pair of units for reference light and measurement light, the size can be 5 mm (length)×8 mm (width)×3 mm (thickness), for example. In addition, in a case of employing a structure in which the gaps between the optical filters and the quantum infrared sensor elements are eliminated to bring them in contact with each other, the thickness of the structure can be further reduced to 2 mm or less.

A quantum infrared gas concentration meter can be achieved by use of the quantum infrared sensor employing the aforementioned configuration. Such a quantum infrared gas concentration meter includes an infrared light source arranged at one end in a sample cell forming a flow passage of a measurement target gas, and the infrared sensor of the present invention arranged at the other end in the sample cell. For example, the quantum infrared gas concentration meter selects two wavelengths by a bandpass filter (center wavelength of 4.3 µm, half bandwidth of 270 nm and transmittance of not less than 75%) matching the absorption characteristics of carbon dioxide, and another bandpass filter (center wavelength of 3.8 µm, half bandwidth of 245 nm and transmittance of not less than 75%) transmitting infrared rays of a wavelength as reference light. The selected infrared rays are detected by the respective infrared sensor elements in the quantum infrared gas concentration meter.

Example 2

Figure 4A:
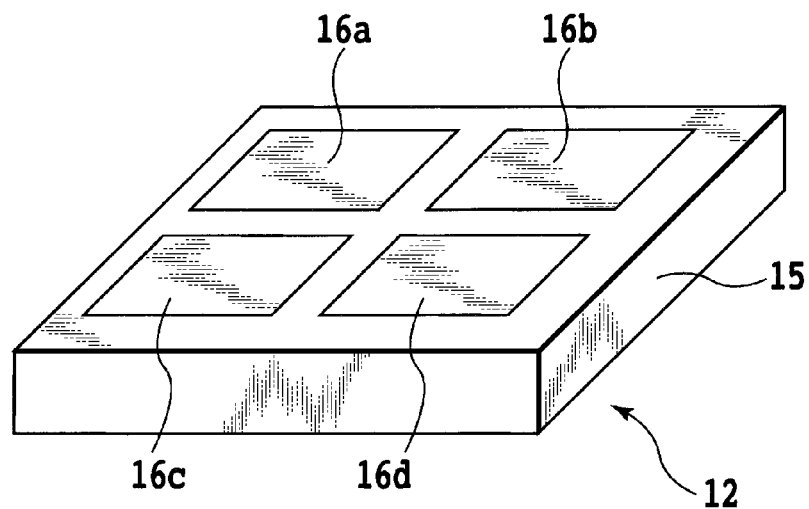
FIG. 4A is a configuration diagram of a quantum infrared sensor according to the present invention in Example 2 and is a top perspective view.
Figure 4B:
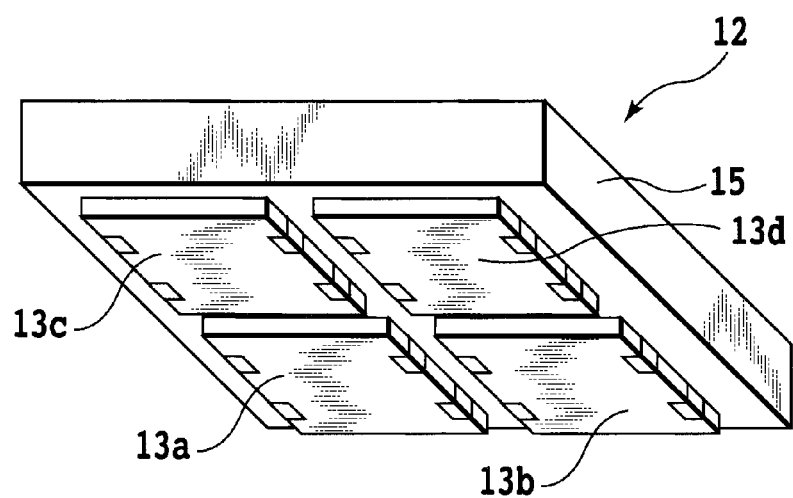
FIG. 4B is a configuration diagram of the quantum infrared sensor according to the present invention in Example 2 and is a bottom perspective view.
Figure 5A:
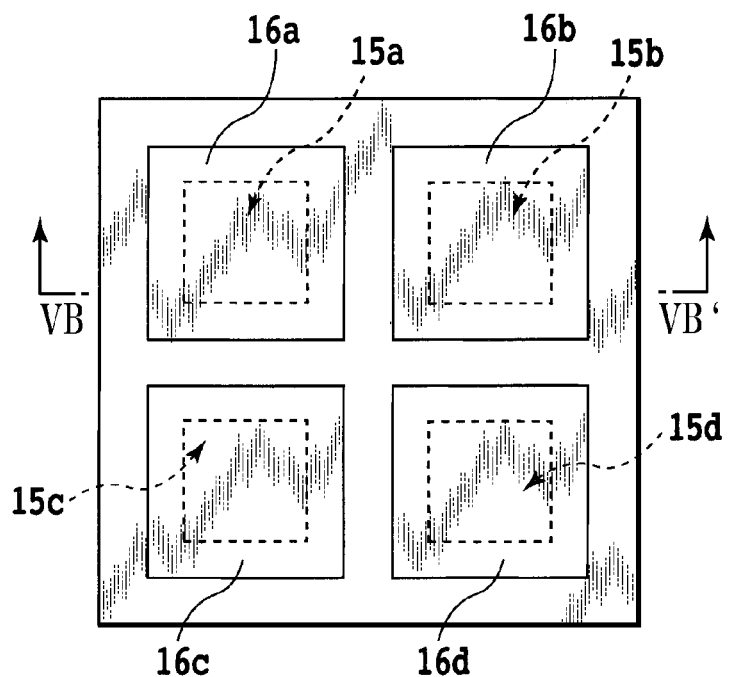
FIG. 5A is a configuration diagram of the quantum infrared sensor according to the present invention in Example 2 and shows a top view thereof.
Figure 5B:
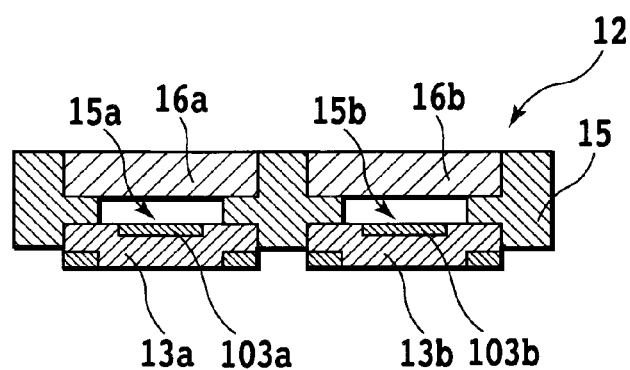
FIG. 5B is a configuration diagram of the quantum infrared sensor according to the present invention in Example 2 and shows a cross-sectional view thereof.
Figure 5C:
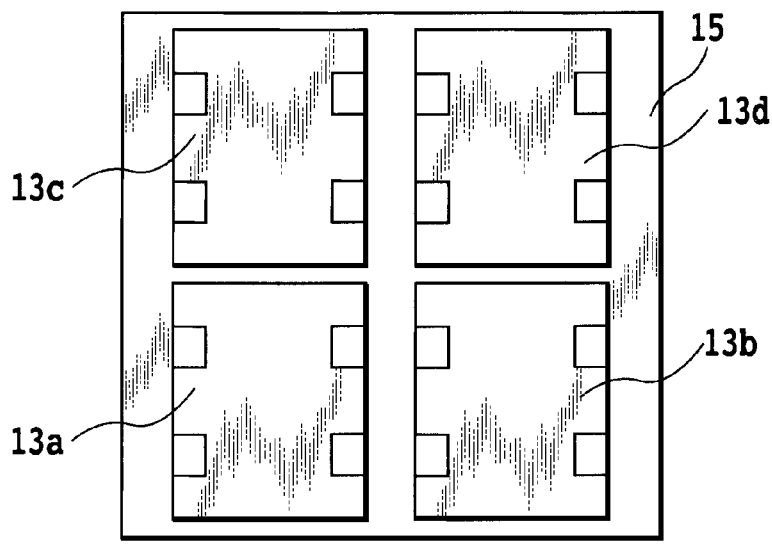
FIG. 5C is a configuration diagram of the quantum infrared sensor according to the present invention in Example 2 and shows a bottom view thereof.

FIGS. 4A and 4B and FIGS. 5A to 5C are configuration diagrams of a quantum infrared sensor according to the present invention in the case of Example 2. FIG. 4A is a top perspective view, and FIG. 4B is a bottom perspective view. FIGS. 5A to 5C show top, cross-sectional and bottom views, respectively. Note that, FIG. 5B is a cross-sectional view taken along the line VB-VB' in FIG. 5A. In the drawings, reference signs 13a to 13d denote quantum infrared sensor elements, respectively, and reference signs 16a to 16d denote optical filters, respectively.

Example 2 illustrates an example in which four quantum infrared sensor elements and four optical filters are employed, the elements and filters employed in Example 1 shown in FIGS. 1A and 1B and FIGS. 2A to 2C.

The four optical filters 16a to 16d are formed of one optical filter that transmits reference light from the infrared light source, and three optical filters that transmit light rays in wavelength ranges each different from that of the reference light.

The same configuration as that described in Example 1 can be employed in Example 2, and the configuration can be applied to an infrared concentration meter as a matter of course. Example illustrates an example where concentrations of three different gas types can be measured.

As described above, with the configuration of Example 1 or 2 of the present invention, a quantum infrared sensor for an NOIR gas sensor and a quantum infrared gas concentration meter using the same can be achieved, the quantum infrared sensor having a small and simple device shape and also being capable of performing stable measurement against disturbance changes such as changes in the flow amount and temperature of gas to be measured.

Example 3

Figure 6:
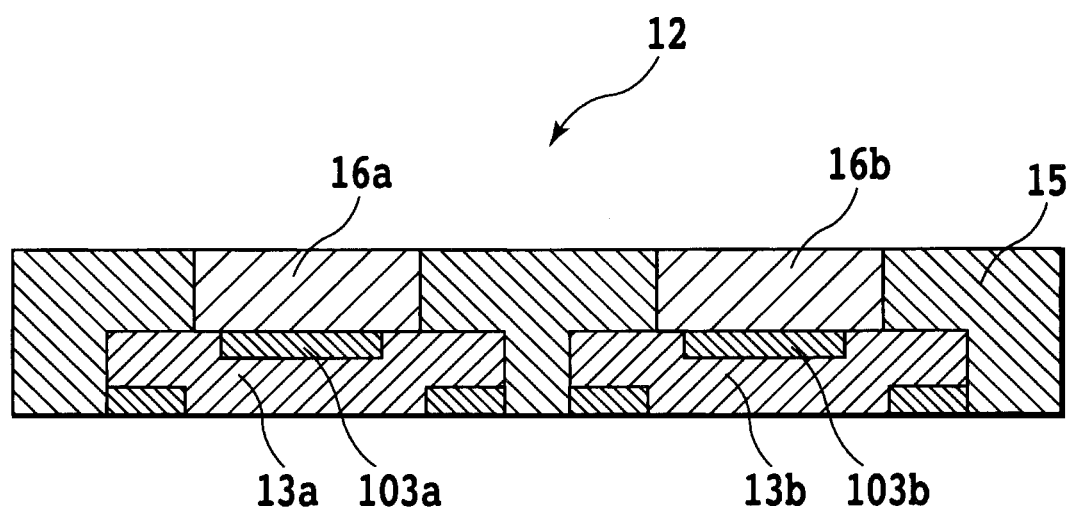
FIG. 6 is a configuration diagram showing a case where spaces between optical filters and quantum infrared sensor elements shown in FIGS. 2B and 5B are eliminated.

FIG. 6 is a configuration diagram without the gaps between the optical filters and the quantum infrared sensor elements shown in FIG. 2B and FIG. 5B. That is, it is possible to employ a structure in which the optical filters 16a and 16b and the quantum infrared sensor elements 13a and 13b are arranged in close contact with each other while the gaps therebetween are eliminated. In addition, the optical filters 16a and 16b can be attached to the holding frame 15 after the quantum infrared sensor elements 13a and 13b are attached to the holding frame 15. With the quantum infrared sensor according to the present invention, no gaps need to be provided between the optical filters 16a and 16b and the quantum infrared sensor elements 13a and 13b as in the case of Example 3. Accordingly, an infrared sensor further reduced in size and thickness can be achieved.

Example 4

Figure 7:
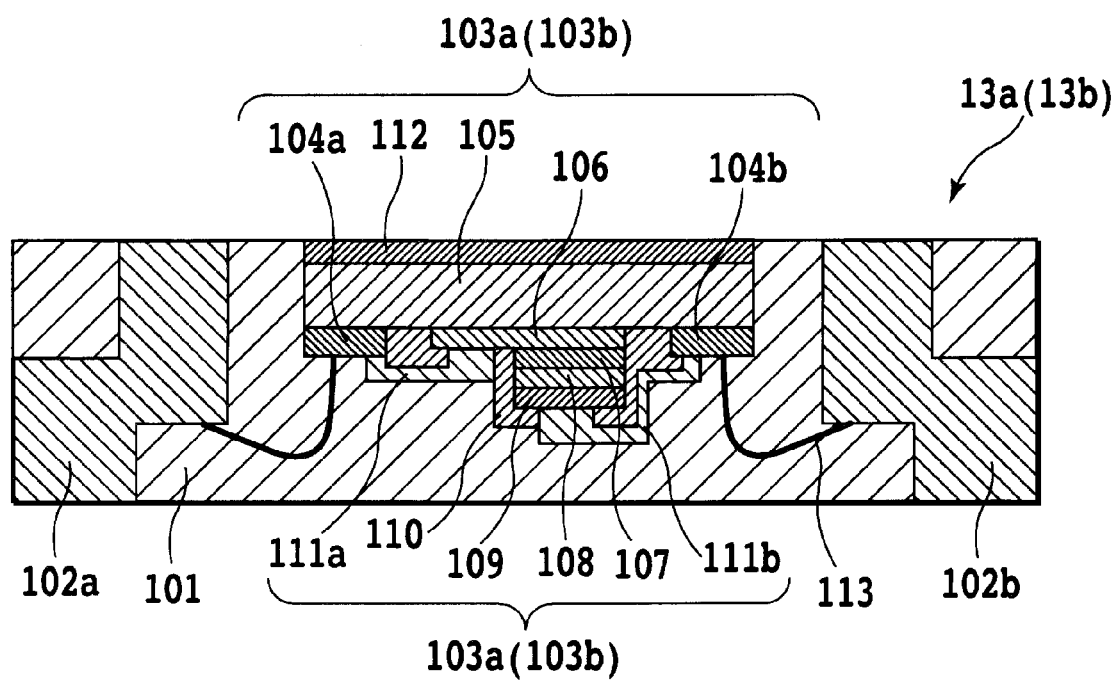
FIG. 7 is a specific configuration diagram of the quantum infrared sensor element shown in FIG. 2B.

FIG. 7 is a specific configuration diagram of one of the quantum infrared sensor elements shown in FIG. 2B. Reference sign 103a (103b) denotes a sensor element portion. The quantum infrared sensor element 13a (13b) includes a sensor element portion 103a (103b). The sensor element portion 103a (103b) includes a first contact layer 106 provided on a substrate 105, an absorption layer 107 provided on the first contact layer 106, a barrier layer 108 provided on the absorption layer 107, a second contact layer 109 provided on the barrier layer 108, a second element electrode 111b provided on the second contact layer 109, a passivation layer 110 provided adjacent to the first contact layer 106, the absorption layer 107, the barrier layer 108 and the second contact layer 109, and a first element electrode 111a provided on the substrate 105 via the passivation layer 110.

Specifically, the sensor element portion 103a (103b) is entirely covered by resin mold 101 except for the light receiving surface thereof, and sensor electrode terminals 102a and 102b for extracting sensor signals are provided respectively on both sides of the sensor element portion 103a (103b). Further, the sensor element portion 103a (103b) is arranged in a state where a window is opened from a part of the resin mold 101 so as to receive infrared rays. Further, pad electrodes 104a and 104b formed on the substrate 105 are connected respectively to the first and second element electrodes 111a and 111b forming the sensor element portion 103a (103b). In addition, the pad electrodes 104a and 104b are electrically connected to the sensor electrode terminals 102a and 102b by wire bondings 113, respectively.

Further, the sensor element portion 103a (103b) will be described in more detail. For example, on a semi-insulating GaAs substrate 105, there are formed sequentially an n-type InSb contact layer 106, an n-type InSb absorption layer 107, a p-type AlInSb barrier layer 108 and a p-type InSb contact layer 109. The n-type InSb contact layer 106 is electrically connected to the pad electrode 104a on one side by the element electrode 111a. Further, the p-type InSb contact layer 109 is electrically connected to the pad electrode 104b on the other side by the element electrode 111b.

The materials of the semiconductor thin films forming the sensor element portion 103a (103b) are not limited to the materials described in the aforementioned example. The passivation film 110 made of SiN or the like is formed at a predetermined position so as to prevent the element electrodes 111a and 111b from being in contact with the semiconductor layers. Further, a protection film 112 is formed on the rear surface of the semi-insulating GaAs substrate 105 because the rear surface serves as a window to receive infrared rays. The protection film 112 is provided for anti-reflection of incident infrared rays and also protection of the sensor portion. A material that transmits infrared rays of a measurement target wavelength as much as possible is preferably selected. For example, silicon oxide, silicon nitride, titanium oxide or the like is preferably used. The film thickness of the protection film is preferably not less than 50 nm but not greater than 800 nm, and more preferably, not less than 100 nm but not greater than 500 nm.

With this configuration, infrared rays having passed through the optical filters 16a and 16b enter the semi-insulating GaAs substrate 105 from the protection films 112 of the sensor element portions 103a and 103b, respectively. The infrared rays having passed through the optical filters 16a and 16b are of wavelengths of 3.8 µm, 4.3 µm and the like. The semi-insulating GaAs substrate 105 has a wide energy band gap, so that the infrared rays having passed through the optical filters 16a and 16b pass though the semi-insulating GaAs substrate 105 without being absorbed. The infrared rays having passed through the semi-insulating GaAs substrate 105 are absorbed by the n-type InSb absorption layers 107 of the sensor element portions 103a and 103b. Thus, photo currents are generated in the n-type InSb absorption layers 107 by photo-excited electrons. Thus, an output voltage can be extracted from each of the element electrodes 111a and 111b according to the amount of the generated photocurrent.

Figure 8:
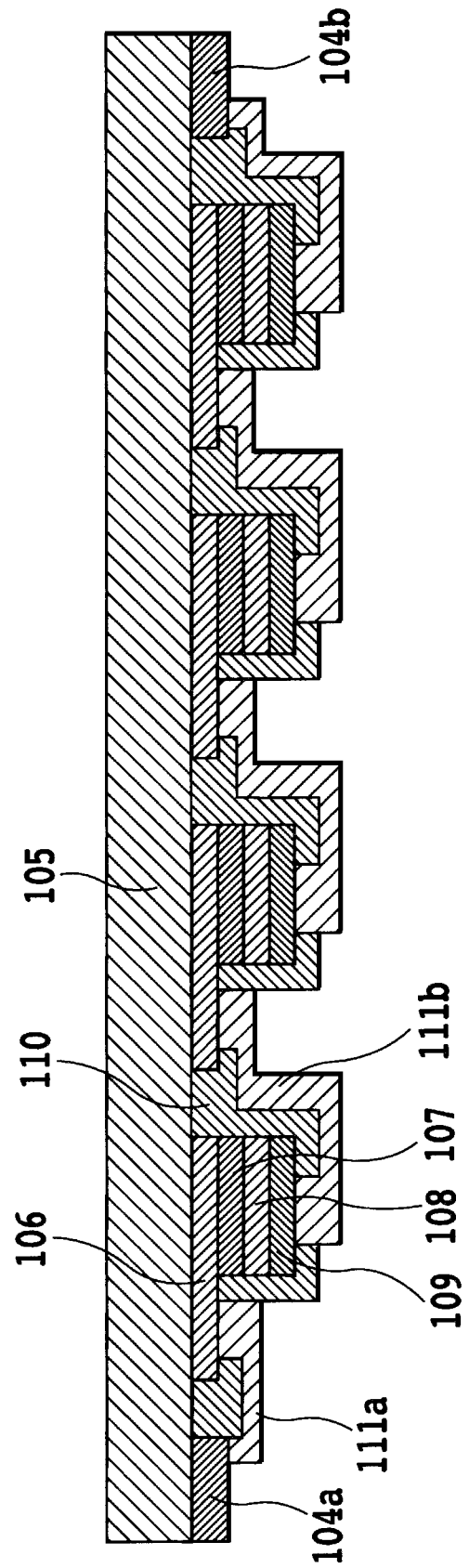
FIG. 8 is a configuration diagram showing a state where sensor element portions of the quantum infrared sensor elements shown in FIG. 7 are connected in series.

FIG. 8 is a configuration diagram of a structure in which the sensor element portions of the quantum infrared sensor elements shown in FIG. 7 are connected in series. In FIG. 8, multiple sensor element portions 103a (103b) are provided, and the multiple sensor element portions 103a (103b) are connected in series. With this structure, a larger output signal can be obtained. Regarding the number of the sensor element portions 103a (103b), it is preferable to form the sensor element portions 103a (103b) as many as possible by utilizing a micro-fabrication technology because the sensitivity of the quantum infrared sensor improves when as many sensor element portions 103a (103b) are connected in series on a substrate having the same area.

Example 5

Figure 9:
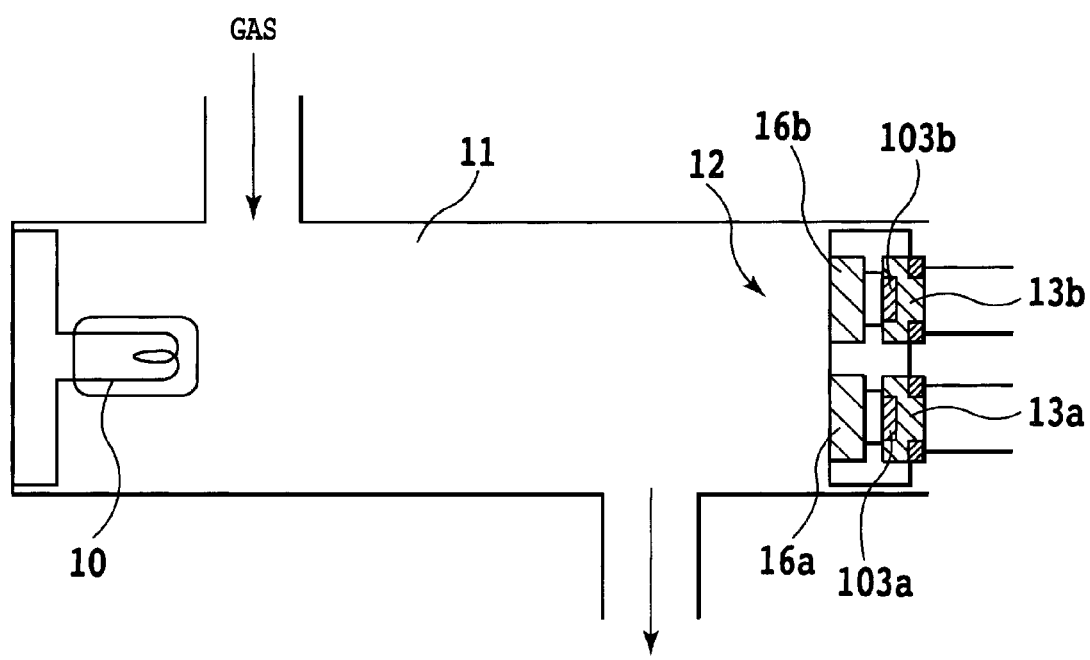
FIG. 9 is a configuration diagram for describing an NDIR gas concentration meter according to the present invention.

FIG. 9 is a configuration diagram for describing the NDIR gas concentration meter of the present invention. The NDIR gas concentration meter is an NDIR gas concentration meter using one light source and two-wavelength comparison technique. For example, the NDIR gas concentration meter selects two wavelengths by the optical filter 16b (center wavelength of 4.3 µm, half bandwidth of 270 nm and transmittance of not less than 75%) matching the absorption characteristics of carbon dioxide, and the optical filter 16a transmitting an infrared ray of a wavelength non-absorbable by various gases, as reference light, e.g., a wavelength near about 3.8 µm. The selected infrared rays are then detected by the respective quantum infrared sensor elements 13a and 13b. In this case, a change with time in the output signal due to deterioration of the light source 10, a dirt on the sample cell 11 or the like can be corrected by a comparison with the absorption characteristics of the measured reference light.

As an example of the NDIR gas concentration meter of the present invention, a 4.3-µm bandpass filter having carbon dioxide absorption characteristics may be used as the optical filter 16b in a carbon dioxide gas concentration meter. In addition, a 4.6-µm bandpass filter having carbon monoxide absorption characteristics is used as the optical filter 16b in a carbon monoxide gas concentration meter. Further, as the optical filter 16b, a 5.2 µm bandpass filter is used for nitrogen oxide (ex. NO), or a 5.6-µm bandpass filter is used for formaldehyde. Thus, a gas concentration meter for the corresponding type of gas can be achieved. A quantum infrared sensor using an optical filter for reference light and optical filters for three different gas types is shown in Example 2 (FIG. 9). According to Example 2, a very small and thin quantum infrared sensor can be achieved, and also the entire NDIR gas concentration meter can be made smaller than ever before.

Figure 10:
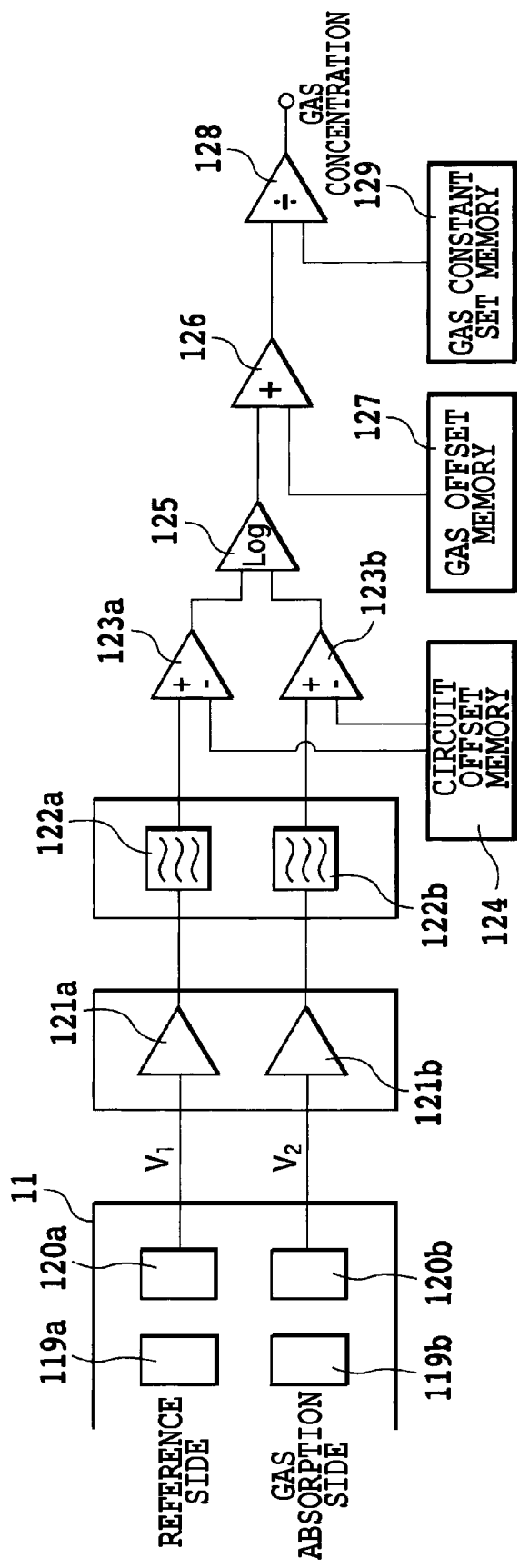
FIG. 10 is a circuit diagram showing a signal processing configuration of the NDIR gas concentration meter shown in FIG. 9.

FIG. 10 is a circuit diagram showing a signal processing configuration of the NDIR gas concentration meter shown in FIG. 9. The NDIR gas concentration meter of the present invention can determine the quantity of gas concentration of a measurement target gas by the following arithmetic operation. According to Lambert-Beer law, gas concentration c can be expressed by the following equation, where $I_{g0}$ denotes the incident light intensity of the gas absorption band, $I_g$ denotes the transmission light intensity of the gas absorption band, $\epsilon$ denotes the light absorption coefficient, and L denotes the length of the gas passage.

$$c = \frac{\log\frac{I_{g0}}{I_g}}{\varepsilon \cdot L} \quad \text{[Equation 1]}$$

The incident light intensity $I_{g0}$ of the gas absorption band is proportional to a transmission light intensity $I_b$ of a wavelength range with no absorption. Thus, when the proportional coefficient is $\alpha$, then $$I_{g0} = \alpha \cdot I_b \quad \text{[Equation 2]}$$

Accordingly, the quantity of the gas concentration can be determined by the following equation using the transmission light amount in the gas absorption band and the transmission light amount in the wavelength range non-absorbable by the gas.

$$c = \frac{\log\frac{I_b}{I_g} + \log\alpha}{\varepsilon \cdot L} \quad \text{[Equation 3]}$$

In a case of using a sensor outputting a value proportional to the light amount of infrared rays by use of the arithmetic method, the signal processing circuit is configured as shown in FIG. 10. Specifically, quantum infrared sensor elements 120a and 120b are provided on the reference side and the gas absorption side via filters 119a and 119b, respectively, at the other end in the sample cell 11. Sensor signals (reference side V1 and gas absorption side V2) from the respective quantum infrared sensor elements 120a and 120b are amplified via amplifiers 121a and 121b. In this case, voltage amplifiers are used when the sensor outputs are voltages, and current-voltage conversion amplifiers are used when the sensor outputs are currents.

Noise filters 122a and 122b remove sensor, circuit and external noises from the sensor signals outputted from the amplifiers 121a and 121b. Low pass filters or bandpass filters for limiting bands, integrators for averaging the signals, or the like are used for the noise filters 122a and 122b.

The signals respectively from the noise filters 122a and 122b and signals from a circuit offset memory 124 are inputted to subtractors 123a and 123b, and the values from the circuit offset memory 124 are subtracted from the sensor signals to remove offsets. The subtractors 123a and 123b are provided for removal of the offsets of the sensors or circuit, but the offsets of the signals can be removed by subtracting, from the sensor signals, the values from the circuit offset memory 124, which are set by updating the values previously or periodically during the operation to determine quantity.

A Log arithmetic unit 125 computes a Log ratio of the signal (V1) of the transmission light amount in the gas absorption band to the signal (V2) of the transmission light amount in the wavelength range non-absorbable by the gas, on the basis of the respective signals from the subtractors 123a and 123b. An adder 126 adds an offset Log $\alpha$ corresponding to the proportional coefficient from the gas offset memory 127 because of usage of the two wavelength ranges to the signal from the Log arithmetic unit 125. A divider 128 performs division of the signal from the adder 126 by the light absorption coefficient $\varepsilon$ from a gas constant set memory 129 and a constant corresponding to the gas passage length L.

Accordingly, by using the equation below, a quantitative analysis of gas concentration can be conducted using the transmission light amount in the absorption band of the gas and the transmission light amount in the wavelength range non-absorbable by the gas.

$$c = \frac{\log\frac{V1}{V2} + \log\alpha}{\varepsilon \cdot L} \quad \text{[Equation 4]}$$

Here, $\alpha = V2'/V1$, $\alpha$ denotes the proportional coefficient, V1 denotes the output voltage on the reference side, V2 denotes the output voltage on the gas absorption side, V2' denotes the voltage value when there is no absorption on the gas absorption side, $\varepsilon$ denotes the absorption coefficient, and L denotes the gas passage length.

Note that, the signal processing portion from the aforementioned subtractors 123a and 123b to the divider 128 may convert signals into digital signals by use of an A/D converter and then process the signals by use of an arithmetic unit such as a CPU, other than analog processing.

Industrial Applicability

The present invention relates to a quantum infrared sensor and a quantum infrared gas concentration meter using the same. According to the present invention, a quantum infrared sensor for an NDIR gas concentration meter and a quantum infrared gas concentration meter using the same can be achieved, the quantum infrared sensor having a small, thin and simple device shape and also being capable of performing stable measurement against disturbance changes such as changes in the flow amount and temperature of gas to be measured.

The invention claimed is:

1. A quantum infrared sensor comprising:
    a plurality of quantum infrared sensor elements;
    a plurality of optical filters providing closer to an infrared light source than are the plurality of quantum infrared sensor elements, and selectively transmitting infrared rays in specific different wavelength ranges, respectively; and
    a holding frame holding at least the optical filters, and includes a plurality of through holes extending from the respective quantum infrared sensor elements toward the infrared light source, wherein
    the quantum infrared sensor elements and the filters are fitted into the through holes of the holding frame, and
    the optical filters and the quantum infrared sensor elements directly contact each other.

2. The quantum infrared sensor according to claim 1, wherein
    the holding frame comprises a multilevel structure with a lower level and an upper level, and the multilevel structure including first and second through holes for receiving infrared rays providing at each of the lower level and the upper level, the first and second through holes facing the quantum infrared sensor elements, respectively,
    first and second quantum infrared sensor elements providing at the lower level, and
    first and second optical filters providing at the upper level while facing the first and second quantum infrared sensor elements, respectively.

3. The quantum infrared sensor according to claim 2, wherein the optical filters are formed of a pair of an optical filter transmitting reference light from the infrared light source, and an optical filter transmitting light in a wavelength range different from that of the reference light.

4. The quantum infrared sensor according to claim 2, wherein the optical filters are formed of an optical filter transmitting the reference light from the infrared light source, and a plurality of optical filters transmitting light rays in wavelength ranges each different from that of the reference light.

5. The quantum infrared sensor according to claim 2, wherein the holding frame is formed of a previously molded package member.

6. The quantum infrared sensor according to claim 1, wherein the optical filters are formed of a pair of an optical filter transmitting reference light from the infrared light source, and an optical filter transmitting light in a wavelength range different from that of the reference light.

7. The quantum infrared sensor according to claim 6, wherein the optical filters are formed of an optical filter transmitting the reference light from the infrared light source, and a plurality of optical filters transmitting light rays in wavelength ranges each different from that of the reference light.

8. The quantum infrared sensor according to claim 6, wherein the holding frame is formed of a previously molded package member.

9. The quantum infrared sensor according to claim 1, wherein the optical filters are formed of an optical filter transmitting the reference light from the infrared light source, and a plurality of optical filters transmitting light rays in wavelength ranges each different from that of the reference light.

10. The quantum infrared sensor according to claim 9, wherein the holding frame is formed of a previously molded package member.

11. The quantum infrared sensor according to claim 1, wherein the holding frame is formed of a previously molded package member.

12. The quantum infrared sensor according to claim 11, wherein the package member is formed so as to be surface-mountable by use of a terminal for surface mounting, which is provided to each of the quantum infrared sensor elements.

13. The quantum infrared sensor according to claim 1, wherein
each of the quantum infrared sensor elements has a sensor element portion, and the sensor element portion comprises:
a first contact layer provided on a substrate;
an absorption layer provided on the first contact layer;
a barrier layer provided on the absorption layer;
a second contact layer provided on the barrier layer;
a second electrode provided on the second contact layer;
a passivation layer provided adjacent to the first contact layer, the absorption layer, the barrier layer and the second contact layer; and
a first electrode provided on the substrate via the passivation layer.

14. The quantum infrared sensor according to claim 1, wherein each of the quantum infrared sensor elements has a sensor element portion, and the sensor element portion comprises:
a first contact layer provided on a substrate;
an absorption layer provided on the first contact layer;
a barrier layer provided on the absorption layer;
a second contact layer provided on the barrier layer;
a second electrode provided on the second contact layer;
a passivation layer provided adjacent to the first contact layer, the absorption layer, the barrier layer and the second contact layer; and
a first electrode provided on the substrate via the passivation layer.

15. The quantum infrared sensor according to claim 14, wherein the first contact layer is made of n-type InSb, the absorption layer is made of p-type doped InSb, the barrier layer is made of p-type AlInSb, and the second contact layer is made of p-type InSb.

16. The quantum infrared sensor according to claim 14, wherein the quantum infrared sensor elements has a plurality of the sensor element portions, and the plurality of the sensor element portions are connected in series.

17. A quantum infrared gas concentration meter comprising:
an infrared light source arranged at one end in a sample cell forming a flow passage of a measurement target gas;
a quantum infrared sensor arranged at the other end in the sample cell,
subtraction means for receiving sensor signals inputted via amplifiers amplifying sensor signals from the quantum infrared sensors and filters removing noise, and for subtracting signals from a circuit offset memory from the sensor signals to remove offsets, respectively;
arithmetic operation means for computing, on the basis of signals from the subtraction means, a ratio of a transmission light amount in an absorption band of the measurement target gas to a transmission light amount in a wavelength range non-absorbable by the measurement target gas;
addition means for adding, to a signal from the arithmetic operation means, an offset corresponding to a proportional coefficient from a gas offset memory because of usage of two wavelength ranges; and
division means for performing division of a signal from the addition means by a light absorption coefficient of the gas from a gas constant memory and a constant of a gas passage length, wherein
quantity of gas concentration is determined by use of the transmission light amount in the absorption band of the measurement target gas and the transmission light amount in the wavelength range non-absorbable by the measurement target gas; and
wherein the quantum infrared sensor comprises:
a plurality of quantum infrared sensor elements;
a plurality of optical filters providing closer to an infrared light source than are the plurality of quantum infrared sensor elements, and selectively transmitting infrared rays in specific different wavelength ranges, respectively; and
a holding frame holding at least the optical filters, and includes a plurality of through holes extending from the respective quantum infrared sensor elements toward the infrared light source, wherein the quantum infrared sensor elements and the filters are fitted into the through holes of the holding frame.

* * * * *